United States Patent
Niwa et al.

(10) Patent No.: US 11,759,299 B2
(45) Date of Patent: Sep. 19, 2023

(54) DENTAL STEREOLITHOGRAPHY-TYPE THREE-DIMENSIONAL PRINTING MATERIAL FOR PREPARING DENTAL THREE-DIMENSIONAL MODELED OBJECT

(71) Applicant: SHOFU INC., Kyoto (JP)

(72) Inventors: Namiki Niwa, Kyoto (JP); Hidefumi Fujimura, Kyoto (JP)

(73) Assignee: SHOFU INC., Kyoto (JP)

( * ) Notice: Subject to any disclaimer, the term of this patent is extended or adjusted under 35 U.S.C. 154(b) by 563 days.

(21) Appl. No.: 16/829,212

(22) Filed: Mar. 25, 2020

(65) Prior Publication Data
US 2020/0390527 A1    Dec. 17, 2020

(30) Foreign Application Priority Data
Mar. 26, 2019    (JP) .................. 2019-057540

(51) Int. Cl.
| | |
|---|---|
| *A61C 13/00* | (2006.01) |
| *C08F 2/50* | (2006.01) |
| *C08F 20/16* | (2006.01) |
| *C08F 20/20* | (2006.01) |
| *C08F 22/12* | (2006.01) |
| *B33Y 10/00* | (2015.01) |
| *B33Y 70/00* | (2020.01) |
| *B33Y 80/00* | (2015.01) |
| *B33Y 40/20* | (2020.01) |

(52) U.S. Cl.
CPC ...... *A61C 13/0019* (2013.01); *A61C 13/0013* (2013.01); *C08F 2/50* (2013.01); *C08F 20/16* (2013.01); *C08F 20/20* (2013.01); *C08F 22/12* (2013.01); *B33Y 10/00* (2014.12); *B33Y 40/20* (2020.01); *B33Y 70/00* (2014.12); *B33Y 80/00* (2014.12)

(58) Field of Classification Search
CPC ...... C08F 220/30; C08F 220/18; C08F 22/12; C08F 20/20; C08F 20/16; C08F 2/50; C08F 2/44; B33Y 80/00; B33Y 70/00; B33Y 40/20; B33Y 10/00; B29L 2031/7536; A61K 6/62; A61C 13/087; A61C 13/0019; A61C 13/0013; A61C 8/0012

USPC ...................................... 433/201.1
See application file for complete search history.

(56) References Cited

U.S. PATENT DOCUMENTS

| | | | |
|---|---|---|---|
| 5,641,391 A * | 6/1997 | Hunter .............. | C25D 5/02 205/672 |
| 2017/0365484 A1* | 12/2017 | Kotler .............. | H01L 21/3063 |
| 2019/0175455 A1 | 6/2019 | Sakamaki et al. | |

FOREIGN PATENT DOCUMENTS

| | | | |
|---|---|---|---|
| EP | 3 360 907 | 8/2018 | |
| EP | 3360907 A1 * | 8/2018 | ........ A61C 13/0013 |
| EP | 3 494 954 | 6/2019 | |
| JP | 2016-525150 | 8/2016 | |
| WO | 2014/172716 | 10/2014 | |
| WO | 2018/005900 | 1/2018 | |
| WO | WO-2018005900 A1 * | 1/2018 | ........ A61C 13/0004 |
| WO | 2018/025943 | 2/2018 | |
| WO | WO-2018025943 A1 * | 2/2018 | ............ A61C 13/01 |

OTHER PUBLICATIONS

Extended European Search Report dated Oct. 9, 2020 in corresponding European Patent Application No. 20165629.5.

* cited by examiner

*Primary Examiner* — Matthew M Nelson
(74) *Attorney, Agent, or Firm* — Wenderoth, Lind & Ponack, L.L.P.

(57) ABSTRACT

To provide a dental stereolithography-type three-dimensional printing material in which the total preparing time required from modeling with using a 3D printer to a final curing is short, work efficiency is excellent, temporal shrinkage deformation of a dental three-dimensional modeled object is suppressed and a dimensional accuracy is excellent. The dental stereolithography-type three-dimensional printing material of the present invention comprises at least one or more (a) monofunctional acrylate monomer having an aromatic ring and (b) photopolymerization initiator, wherein an electronegativity difference between adjacent atoms which are bonded by covalent bond in all atoms constituting the (a) monofunctional acrylate monomer having an aromatic ring is less than 1.0.

17 Claims, No Drawings

DENTAL STEREOLITHOGRAPHY-TYPE THREE-DIMENSIONAL PRINTING MATERIAL FOR PREPARING DENTAL THREE-DIMENSIONAL MODELED OBJECT

CROSS-REFERENCE TO RELATED APPLICATIONS

This application is based on and claims the benefit of priority from Japanese Patent Application Serial No. 2019-057540 (filed on Mar. 26, 2019), the contents of which are hereby incorporated by reference in their entirety.

BACKGROUND OF THE INVENTION

Field of the Invention

The present invention relates to a dental stereolithography-type three-dimensional printing material and a preparing method of a dental three-dimensional modeled object using the material of the present invention.

Description of the Related Art

In recent years, by rapidly spreading three-dimensional CAD, a print modeling technology using a 3D printer has been adopted in various industrial fields. Among the print modeling technologies using a 3D printer, the stereolithography system is a method for preparing a three-dimensional modeled object by laminating and curing photo-curable resin (hereinafter, also referred to as stereolithography-type three-dimensional printing material or three-dimensional printing material) for each layer with ultraviolet light and/or visible light based on a three-dimensional CAD data. With the spread of such print modeling technologies, it has become possible to prepare products simply, quickly, and in mass production.

In the print modeling technology of the stereolithography system, many proposals regarding a stereolithography-type three-dimensional printing material aiming for further improvement of work efficiency, modeling accuracy, and mechanical properties are disclosed. For example, Japanese Unexamined Patent Application Publication No. 2018-76455 discloses a printing material which can prepare a modeled object with a small warp change rate, and excellent heat resistance and strength in a short modeling time by including a specific cationic polymerizable compound and a specific radical polymerizable compound.

In the dental field, the usefulness of the print modeling technology is also high. Conventionally, the patient's oral cavity shape has been modeled in the oral cavity by using an impression material, and the cured mold was managed as an actual data which reproduced the oral cavity shape. However, in recent years, intraoral optical scanners have become popular, and it is possible to digitally manage the oral cavity shape as three-dimensional CAD data by scanning the patient's oral cavity shape with the scanner.

In this background, proposals regarding a stereolithography-type three-dimensional printing material have been disclosed in recent year in the field of dental materials.

For example, Japanese Translation of PCT International Application Publication No. 2016-525150 discloses a liquid resin composition which can simply and easily prepare a denture base and an artificial tooth by using a stereolithography-type three-dimensional printer.

SUMMARY OF THE INVENTION

Technical Problem

A dental prosthetic device prepared by using the print modeling technology of the stereolithography system is generally prepared in the order of "modeling by a 3D printer→cleaning of a three-dimensional modeled object→final curing of a three-dimensional modeled object by a light and/or heating type post-curing device".

Because the degree of polymerization of the conventional stereolithography-type three-dimensional printing material at the stage of modeling by a 3D printer is low, there is a problem that the polymerization shrinkage during a final curing by a post-curing device is large, deformation generates, and therefore the product after the final curing is less likely to match the desired data.

In particular, in the dental prosthetic device, because strict precision to match the individual patient is required, it must not generate deformation and must match the desired data of the patient's oral cavity.

An object of the present invention is to provide a dental stereolithography-type three-dimensional printing material in which the total preparing time of a dental three-dimensional modeled object prepared by a 3D printer and temporal deformation of the dental three-dimensional modeled object is suppressed by achieving high polymerization degree at the stage of modeling to exhibit excellent dimensional accuracy.

Solution to Problem

The present invention provides a dental stereolithography-type three-dimensional printing material comprising at least one or more (a) monofunctional acrylate monomer having an aromatic ring and (b) photopolymerization initiator, wherein an electronegativity difference between adjacent atoms which are bonded by covalent bond in all atoms constituting the (a) monofunctional acrylate monomer having an aromatic ring is less than 1.0.

In the present invention, it is preferable that the content of the (b) photopolymerization initiator base on the total weight of the (a) monofunctional acrylate monomer having an aromatic ring and the (b) photopolymerization initiator is within a range of 0.1 to 5 wt. %.

In the present invention, it is preferable that the dental stereolithography-type three-dimensional printing material further comprises (c) polyfunctional methacrylate monomer wherein an electronegativity difference between adjacent atoms which are bonded by covalent bond in all atoms constituting the (c) polyfunctional methacrylate monomer is less than 1.0, and the (c) polyfunctional methacrylate monomer satisfies the following formula (I).

$$\text{Molecular weight/molecular length when both ends of the monomer molecule are methacrylate groups (angstrom)} < 20.0 \quad \text{Formula (I)}$$

In this case, it is preferable that the dental stereolithography-type three-dimensional printing material comprises, based on the total weight of the (a) monofunctional acrylate monomer having an aromatic ring, the (b) photopolymerization initiator and the (c) polyfunctional methacrylate monomer, (a) monofunctional acrylate monomer having an aromatic ring: 10 to 70 wt. %, (b) photopolymerization initiator: 0.1 to 5 wt. %, and (c) polyfunctional methacrylate monomer: 25 to 89.9 wt. %.

In the present invention, it is preferable that the dental stereolithography-type three-dimensional printing material further comprises at least one selected from a group consisting of a non-dendritic polymer containing no inorganic atom in the structure, an inorganic filler, and a coloring material.

In the present invention, it is preferable that the dental stereolithography-type three-dimensional printing material has a viscosity (mPa·s) at 23° C. within a range of 1 to less than 3000.

The present invention provides a preparing method of a dental three-dimensional modeled object, wherein the method does not comprise a step of a final curing a dental three-dimensional modeled object, by a light and/or heating type post-curing device, prepared by arbitrary stereolithography-type three-dimensional printing machine on the recommended conditions using the dental stereolithography-type three-dimensional printing material of the present invention.

Advantageous Effects of Invention

The present invention can provide a dental stereolithography-type three-dimensional printing material in which the preparing time required from modeling by using a 3D printer to a final curing is short therefore work efficiency is excellent, and temporal deformation of the dental three-dimensional modeled object is less likely caused and therefore dimensional accuracy is excellent.

DETAILED DESCRIPTION OF THE PREFERRED EMBODIMENTS

The numerical range represented by using "-" in the present specification means a range including the numerical values before and after "-" as the lower limit value and the upper limit value.

In the present invention, "dental stereolithography-type three-dimensional printing material" means a material for preparing a modeled object having three-dimensional shape used in a dentistry (hereinafter, also referred to as a dental three-dimensional modeled object) by a stereolithography-type printing mechanism.

The term "modeled object having three-dimensional shape used in a dentistry" means a devices, an equipment or an instrument used inside and outside of the oral cavity in dentistry, and specific examples include a prosthetic device, an orthodontic device, a model, a splint, a mouse guard, a night guard, a surgical guide, a cast for casting, and the like. The term "prosthesis device" means an artificial structure which replaces a natural tooth, and specific examples include an inlay, an onlay, a crown, a bridge, an artificial tooth and the like.

Among these, it is preferable to use the dental stereolithography-type three-dimensional printing material of the present invention for preparing a model, a splint, a mouth guard, a night guard, a surgical guide, and a cast for casting.

The term "stereolithography-type printing mechanism" means a three-dimensional modeling method using a 3D printer which uses ultraviolet light and/or visible light as a light source, and specific examples include SLA (Stereo Lithography Apparatus) method, DLP (Digital Light Processing) method, an inkjet method, and the like.

The term "SLA method" means a method for preparing a three-dimensional modeled object by irradiating the three-dimensional printing material with a dotted laser light.

When a dental three-dimensional modeled object is prepared by SLA method, for example, the three-dimensional printing material of the present invention is stored in a tank, and the liquid surface of the three-dimensional printing material is selectively irradiated with dotted laser light to cure the three-dimensional printing material, and a cured layer having a desired thickness is formed on a stage for modeling for obtaining a desired shape. Then, the stage for modeling is lowered, uncured three-dimensional printing material in amount of one layer is supplied on the cured layer, and the layer is cured in the same manner and this laminating operation to obtain a continuous cured layer is repeated. Thereby, the dental three-dimensional modeled object can be prepared.

The term "DLP method" means a method for preparing a three-dimensional modeled object by irradiating the three-dimensional printing material with a planar light.

When a dental three-dimensional modeled object is prepared by DLP method, for example, the three-dimensional printing material of the present invention is stored in a tank, and three-dimensional printing material is selectively irradiated with planar light from the bottom surface of the tank to cure the three-dimensional printing material, and a cured layer having a desired thickness is formed on a stage for modeling for obtaining a desired shape. Then, the stage for modeling is raised, uncured three-dimensional printing material in amount of one layer is supplied under the cured layer, and the layer is cured in the same manner and this laminating operation to obtain a continuous cured layer is repeated. Thereby, the dental three-dimensional modeled object can be prepared.

The term "inkjet method" means a method of obtaining the three-dimensional molded object by continuously discharging droplets of a three-dimensional printing material to a substrate from an inkjet nozzle and irradiating the droplets attached to the substrate with a light.

When a dental three-dimensional modeled object is prepared by inkjet method, for example, while scanning a head having an inkjet nozzle and a light source in a plane, the inkjet nozzle discharges the three-dimensional printing material to a substrate and the discharged three-dimensional printing material is irradiated with light to form a cured layer. By repeating these operations, the cured layers are sequentially laminated. Thereby, the dental three-dimensional molded object can be prepared.

It is preferable that the dental stereolithography-type three-dimensional printing material of the present invention has a viscosity at 23° C. within a range of 1 (mPa·s) to less than 3000 (mPa·s) from the viewpoint of the suitability in the stereolithography and the easy cleaning.

The "(a) monofunctional acrylate monomer having an aromatic ring" of the present invention is a monomer containing only one acrylate group and has an aromatic ring in the structure of the monomer.

It is preferable that "aromatic ring" is a benzene ring. The aromatic ring may be located anywhere in the structure, but a benzene ring is preferably presence at the end.

Especially, in the "(a) monofunctional acrylate monomer having an aromatic ring" of the present invention, an electronegativity difference between adjacent atoms which are bonded by covalent bond in all atoms constituting the (a) monofunctional acrylate monomer having an aromatic ring is less than 1.0.

The term "covalent bond" of the present invention means a chemical bond which involves a share of an electron pair between atoms and does not include intermolecular forces such as hydrogen bond, Coulomb force, dipole interaction, and Van der Waals force.

The term "electronegativity" means a scale that relatively indicates the strength of an atom in a molecule attracting an electron. The electronegativity of the present invention follows Pauling's electronegativity.

When electronegativity difference between adjacent atoms which are bonded by covalent bond is 1.0 or more, modeling defect is likely to occur in case of performing stereolithography under the same conditions as the case of less than 1.0, and as a result, an extension of the modeling time or a treatment such as heating materials is necessary, which causes a decrease in modeling efficiency.

The term "modeling defect" means that the curing of the three-dimensional printing material is insufficient, and specific examples include that a modeled object is not prepared, the modeled object is not finished in a desired shape, the laminated line on the surface of the modeled object is unclear, and the like.

Specific examples of the "(a) monofunctional acrylate monomer having an aromatic ring" of the present invention include ethoxylated o-phenylphenol acrylate (A-PP-EO), phenoxydiethylene glycol acrylate (A-P2EG), phenoxy polyethylene glycol acrylate, 3-phenoxybenzyl acrylate (A-PB), phenoxyethyl acrylate (A-PE), neopentyl glycol-acrylic acid-benzoic acid ester and the like.

The three-dimensional printing material of the present invention may contain only one type of "(a) monofunctional acrylate monomer having an aromatic ring" or may contain two or more types thereof.

The content of the "(a) monofunctional acrylate monomer" having an aromatic ring in the three-dimensional printing material of the present invention (the total content in case of two or more kinds) is within a range of 1 to 99.9 wt. %, preferably within a range of 10 to 70 wt. % from the viewpoint of the strength of the modeled object used for the dentistry prepared by the present invention base on the total weight of the (a) monofunctional acrylate monomer having an aromatic ring and the (b) photopolymerization initiator, or (a) monofunctional acrylate monomer having an aromatic ring, the (b) photopolymerization initiator and the (c) polyfunctional methacrylate monomer in the case of containing the (c) polyfunctional methacrylate monomer described below.

The "(b) photopolymerization initiator" of the present invention means a polymerization initiator which absorbs a light with wavelengths generally used in a stereolithography-type 3D printer to generate a radical. Specifically, the polymerization initiator has an absorption band in the wavelength region of 350 to 450 nm.

Specific examples of the "(b) photopolymerization initiator" of the present invention include alkylphenone-based compounds, acylphosphine oxide-based compounds, titanocene-based compounds, oxime ester-based compounds, benzoin-based compounds, acetophenone-based compounds, benzophenone-based compounds, thioxanthone-based compounds, benzyl-based compounds, diphenyl sulfide-based compounds, anthraquinone-based compounds and the like.

Among these, acylphosphine oxide-based compounds are preferable from the viewpoint of reactivity and the like. Specific examples of the acylphosphine oxide-based compounds includes bis (2,4,6-trimethylbenzoyl)-phenylphosphine oxide, 2,4,6-trimethylbenzoyl-diphenyl-phosphine oxide (MAPO) and the like.

The three-dimensional printing material of the present invention may contain only one type of (b) photopolymerization initiator or may contain two or more types thereof.

The content of the "(b) photopolymerization initiator" in the three-dimensional printing material of the present invention (the total content in case of two or more kinds) is preferably within a range of 0.1 to 5 wt. % base on the total weight of the (a) monofunctional acrylate monomer having an aromatic ring and the (b) photopolymerization initiator, or (a) monofunctional acrylate monomer having an aromatic ring, the (b) photopolymerization initiator and the (c) polyfunctional methacrylate monomer in the case of containing the (c) polyfunctional methacrylate monomer described below. When the content of the (b) photopolymerization initiator is less than 0.1 wt. %, a modeling defect due to insufficient curing (decrease in dimensional accuracy of the modeled object, decrease in adsorption of the modeled object and the stage of modeling and the like) may occur, even if the exposure time per layer is set to the upper limit. When the content of the (b) photopolymerization initiator is more than 5 wt. %, a modeling defect due to excessive curing (decrease in dimensional accuracy of the modeled object, decrease in releasability of the modeled object and the tank, and the like) and a failure in the color tone may occur, even if the exposure time per layer is set to the lower limit.

The three-dimensional printing material of the present invention may contain the (c) polyfunctional methacrylate monomer wherein an electronegativity difference between adjacent atoms which are bonded by covalent bond in all atoms constituting the (c) polyfunctional methacrylate monomer is less than 1.0, and the (c) polyfunctional methacrylate monomer satisfies the following formula (I).

Molecular weight/molecular length when both ends of the monomer molecule are methacrylate groups(angstrom)<20.0    Formula (I)

The "(c) polyfunctional methacrylate monomer" of the present invention is a monomer containing two or more methacrylate groups. By containing the "(c) polyfunctional methacrylate monomer", suitable strength as the dental three-dimensional modeled object can be obtained.

The "molecular length when both ends of the monomer molecule are methacrylate groups (angstrom)" of the present invention is calculated from the average bond distance between atoms by covalently bonds in the molecule.

When the value in the formula (I) is 20.0 or more, modeling defect is likely to occur in case of performing stereolithography under the same conditions as the case of less than 20.0, and as a result, an extension of the modeling time or a treatment such as heating materials is necessary, which causes a decrease in modeling efficiency.

Specific examples of the "(c) polyfunctional methacrylate monomer" of the present invention include bisphenol A dimethacrylate, urethane dimethacrylate (UDMA), ethoxylated bisphenol A dimethacrylate, ethylene glycol dimethacrylate, diethylene glycol dimethacrylate, triethylene glycol dimethacrylate (2M-3EG), tetraethylene glycol dimethacrylate, polyethylene glycol dimethacrylate, hexamethylene glycol dimethacrylate, neopentyl glycol dimethacrylate, polypropylene glycol dimethacrylate, ethoxylated polypropylene glycol dimethacrylate and the like.

The three-dimensional printing material of the present invention may contain only one type of the (c) polyfunctional methacrylate monomer, or may contain two or more types thereof.

The content of the "(c) polyfunctional methacrylate monomer" in the three-dimensional printing material of the present invention (the total content in case of two or more kinds) is within a range of 0 to 89.9 wt. %, preferably within a range of 25 to 89.9 wt. % from the viewpoint of the strength of the modeled object used for the dentistry prepared by the present invention base on the total weight of the (a) monofunctional acrylate monomer having an aromatic ring, the (b) photopolymerization initiator and the (c) polyfunctional methacrylate monomer.

If necessary, the three-dimensional printing material of the present invention may contain at least one selected from a group consisting of a non-dendritic polymer containing no inorganic atom in the structure, an inorganic filler, and a coloring material.

The term "non-dendritic polymer containing no inorganic atom in the structure" means an organic polymer containing no inorganic atom in the structure and is not involved in polymerization.

Examples include polymethylmethacrylate, styrene-butadiene copolymer, acrylonitrile-styrene copolymer, acrylonitrile-styrene-butadiene copolymer, polyether ether ketone, polybutadiene, polyethylene terephthalate, polyvinyl chloride, poly(bisphenol A carbonate), polyethylene glycol, methoxy polyethylene glycol, methoxy polyethylene glycol amine, poly (ethylene glycol) methyl ether, poly (ethylene glycol) dimethyl ether, poly (ethylene glycol) bis (carboxymethyl) ether, poly (ethylene glycol) bis (amine), poly (ethylene glycol) divinyl ether, O-(2-aminoethyl) polyethylene glycol, polypropylene glycol, polylactic acid-glycolic acid copolymer, polyglycolic acid, polylactic acid, polydioxanone, poly(1,4-phenylene sulfide) and the like.

The three-dimensional printing material of the present invention may contain only one type of non-dendritic polymer containing no inorganic atom in the structure or may contain two or more types thereof.

Examples of the "inorganic filler" of the present invention include Group I, II, III, IV periodic metals, transition metals or oxides, silicic acid thereof or mixtures thereof.

Specific examples include glass powders such as silicon dioxide (silica) powder, aluminum oxide powder (alumina powder), zirconia powder, lanthanum glass powder, barium glass powder and strontium glass powder, quartz powder, titanium oxide powder, glass beads, glass fibers, barium fluoride powder, silica gel powder, colloidal silica, zirconium oxide powder and the like.

The average particle diameter of the inorganic filler needs to be smaller than the laminate height per layer in the modeled object, and is preferably within a range of 0.001 to 50 μm, more preferably 0.001 to 5 μm.

It is preferable that the inorganic filler is surface treated with a silane coupling agent from the viewpoint of improving dispersibility in the three-dimensional printing material.

Examples of group of the silane coupling agent include an acrylsilyl group, a methacrylsilyl group, an epoxysilyl group, a methylsilyl group, a dimethylsilyl group, a trimethylsilyl group, a methoxysilyl group, a dimethoxysilyl group, a trimethoxysilyl group, an ethoxysilyl group, a diethoxysilyl group, a triethoxysilyl group, an alkylsilyl group, a diphenylsilyl group, a vinylsilyl group, a styrylsilyl group, an organosilyl group, a dimethylpolysiloxane group, a hexamethyldisilazane group, an aminoalkylsilyl group and the like, and one or more of these can be used.

The three-dimensional printing material of the present invention may contain only one type of the inorganic filler or may include two or more types thereof.

The "coloring material" of the present invention is not limited as long as it does not prevent modeling by the stereolithography-type 3D printer and does not easily discolor, and examples thereof include inorganic pigments, oil-soluble dyes, pigments and the like.

The three-dimensional printing material of the present invention may contain only one type of the coloring material or may contain two or more types thereof.

The total content of the non-dendritic polymer containing no inorganic atom in the structure, the inorganic filler and the coloring material is within a range of 50 part by weight or less, preferably within a range of 20 part by weight or less base on the total weight of the (a) monofunctional acrylate monomer having an aromatic ring and the (b) photopolymerization initiator, or (a) monofunctional acrylate monomer having an aromatic ring, the (b) photopolymerization initiator and the (c) polyfunctional methacrylate monomer in the case of containing the (c) polyfunctional methacrylate monomer. When it exceeds 50 part by weight, modeling defect may occur due to increasing viscosity.

The three-dimensional printing material of the present invention may contain a monomer other than the "(a) monofunctional acrylate monomer having an aromatic ring" and the "(c) polyfunctional methacrylate monomer". In this case, the content of the other monomer is preferably smaller than that of "(a) monofunctional acrylate monomer having an aromatic ring", and in case of containing the "(c) polyfunctional methacrylate monomer", is preferably less than that of the "(c) polyfunctional methacrylate monomer". Specifically, the content of the other monomer is within a range of 30 part by weight or less, preferably within a range of 20 part by weight or less, more preferably within a range of 10 part by weight or less. Further, it is preferable that the three-dimensional printing material of the present invention does not contain the other monomer other than "(a) monofunctional acrylate monomer having an aromatic ring" and "(c) polyfunctional methacrylate monomer".

In the preparing method of a dental three-dimensional modeled object of the present invention, it is possible to prepare a dental three-dimensional modeled object by modeling with arbitrary stereolithography-type three-dimensional printing machine recommended parameters using the dental stereolithography-type three-dimensional printing material of the present invention, therefore, it is not necessarily to perform a step of a final curing by a light and/or heating type post-curing device.

The "light and/or heating type post-curing device" means an apparatus or a device for performing post-polymerization of the dental three-dimensional modeled object which is modeled by arbitrary stereolithography-type three-dimensional printing machine, by ultraviolet and/or visible light and/or heat.

Examples ((a) Monofunctional Acrylate Monomer Having an Aromatic Ring)

As the (a) monofunctional acrylate monomer having an aromatic ring, ethoxylated o-phenylphenol acrylate (A-PP-EO), phenoxyethyl acrylate (A-PE), 3-phenoxybenzyl acrylate (A-PB) and phenoxydiethylene glycol acrylate (A-P2EG) were used in the examples.

((c) Polyfunctional Methacrylate Monomer)

As the (c) polyfunctional methacrylate monomer, triethylene glycol dimethacrylate (2M-3EG), ethoxylated bisphenol A dimethacrylate-EO2.6 (2M-2.6EO), ethoxylated bisphenol A dimethacrylate-EO4.0 (2M-4.0EO) and urethane dimethacrylate (UDMA) were used in the comparative examples and the examples.

(Other Monomers)

As other monomers, 2-hydroxy-3-phenoxypropyl acrylate (A-PP-OH), dimethylol-tricyclodecane diacrylate (2A-3cD), phenoxyethyl methacrylate (M-PE) and ethoxylated isocyanuric acid triacrylate (3A-IC) were used in the comparative examples.

((b) Photopolymerization Initiator)

As the (b) photopolymerization initiator, 2,4,6-trimethylbenzoyl-diphenyl-phosphine oxide (MAP 0) was used in the comparative examples and the examples.

(Non-Dendritic Polymer Containing No Inorganic Atom in the Structure)

As the non-dendritic polymer containing no inorganic atom in the structure, polyethylene glycol Mn1000 (PEG1000) and polypropylene glycol Mn4000 (PPG4000) were used in the examples.

(Inorganic Filler)

As the inorganic filler, AEROSIL® R-812 (R-812), which is fine particle silica, manufactured by Nippon Aerosil Co., Ltd. was used in the examples.

(Coloring Material)

As the coloring material, titanium oxide which is a pigment, and Solvent Black 5 which is a dye were used in the examples.

<Preparation of Stereolithography-Type Three-Dimensional Printing Material>

Each component was weighed according to the composition table of Examples (1) to (20) and Comparative Examples (1) to (5) described in following Tables 1 to 3, and the whole amounts were put in a mixing container for a planetary centrifugal mixer (manufactured by THINKY). The stereolithography-type three-dimensional printing material was obtained by mixing at 2000 rpm for 30 minutes with the planetary centrifugal mixer.

<Measurement and Evaluation>

Using the prepared stereolithography-type three-dimensional printing material, the measurements and evaluations were performed as follows. The results are described in the Tables 1-3.

However, the stereolithography-type three-dimensional printing materials of Examples (11) to (12) and Comparative Example (5) were high viscosity under the environment of 23±1° C. and therefore it was difficult to prepare a test specimen used for the following evaluations by modeling with a 3D printer. Therefore, each test specimen was modeled by using the stereolithography-type three-dimensional printing materials of Examples (11) to (12) and Comparative Example (5) heated under environment of 40 to 65° C.

(Measurement of Viscosity)

The prepared stereolithography-type three-dimensional printing material was allowed to stand still for 24 hours in the thermostatic chamber at 23±1° C. After 24 hours still-standing, the viscosity of the stereolithography-type three-dimensional printing material was measured by using a rotary viscometer and is described as the result of the viscosity evaluation.

The lower the viscosity of the stereolithography-type three-dimensional printing material, the easier it is to perform stereolithography and washing of the three-dimensional modeled object, and therefore the work efficiency is excellent. When the viscosity of the stereolithography-type three-dimensional printing material exceeds 3000 (mPa·s), there is a case that the fluidity decreases, and the liquid volume filled in the modeling area for each lamination is insufficient, which results in modeling defect. In order to avoid this, when the stereolithography-type three-dimensional printing material has the viscosity exceeds 3000 (mPa·s), it is possible to reduce the viscosity to reduce modeled defect by preheating or modeling using a 3D printer equipped with a temperature control system. Further, when the viscosity of the stereolithography-type three-dimensional printing material exceeds 10,000 (mPa·s), there is a case that the unreacted stereolithography-type three-dimensional printing material adhering to the dental three-dimensional modeled object cannot be completely removed during the alcohol cleaning and may remain on the surface of the three-dimensional modeled object. It is not preferable to extend the cleaning time because it affects the dimensional accuracy of the dental three-dimensional modeled object. Based on these, in the stereolithography-typr three-dimensional printing material according to the present invention, the result of the viscosity evaluation is preferably less than 10,000 (mPa·s) and is particularly preferably less than 3000 (mPa·s). The criteria for determining the result of the viscosity evaluation are described below.

Evaluation A: 1 (mPa·s) or more and less than 3000 (mPa·s)
Evaluation B: 3000 (mPa·s) or more and less than 10000 (mPa·s)
Evaluation C: 10000 (mPa·s) or more (Measurement of Polymerization Rate)

By using a 3D printer (manufactured by DGSHAPE Corporation; DWP-80S), 3 sheets of modeled objects having the dimension of 10 mm×10 mm×1.2 mm were obtained from the stereolithography-type three-dimensional printing material prepared under the modeling parameters of the laminate height of 50 μm per layer and the exposure time of 8 seconds. The obtained modeled objects were polished into the dimension of 10 mm×10 mm×1.0 mm by a water resistant polishing sheet #2000 to obtain three test specimens for evaluation of the green-state polymerization rate.

The absorbance at a wave number of 4000 to 7000 cm$^{-1}$ of the liquid stereolithography-type three-dimensional printing material and the test specimens for evaluation of the green-state polymerization rate were measured by FT-IR. The C=C peak intensity ratio was calculated by the following formula (II) from the C=C-derived peak absorbance (wave number: around 6160 cm$^{-1}$) and the base peak absorbance (wave number: around 4925 cm$^{-1}$ or around 4680 cm$^{-1}$).

"C=C peak intensity ratio"="C=C derived peak absorbance/base peak absorbance"  Formula (II)

The polymerization rate was calculated by the following formula (III) from the C=C peak intensity ratio of the liquid stereolithography-type three-dimensional printing material and the test specimens for evaluation of the green-state polymerization rate, and the average value of the three sheets of the test specimens for evaluation of the green-state polymerization rate was used as the evaluation result of the green-state polymerization rate.

Polymerization rate (%)=(1-"C=C peak intensity ratio of a green-state test specimen"/"C=C peak intensity ratio of liquid material")×100  Formula (III)

By using the LC-3D print Box (manufactured by Nextdent B.V.) which is a post-curing device, the test specimens for evaluation of the green-state polymerization rate after measurement was finally cured for 15 minutes to obtain three test specimens for evaluation of the post-final curing polymerization rate. The absorbance of the test specimens for evaluation of the post-final curing polymerization rate were measured by FT-IR as well as the test specimens for evaluation of the green-state polymerization rate to calculate the polymerization rate. The average value of the three test specimens for evaluation of the post-final curing polymerization rate was used as the evaluation result of the post-final curing polymerization rate.

From the evaluation results of the green-state and the post-final curing polymerization rate, the polymerization increase rate (%) was calculated by the following formula (IV).

Polymerization increase rate (%)=("evaluation result of post-final curing polymerization rate"–"evaluation result of green-state polymerization rate")/"evaluation result of post-final curing polymerization rate"×100   Formula (IV)

In the dental three-dimensional modeled object prepared by steps from stereolithography through final curing, the closer the green-state polymerization rate is to the post-final curing polymerization rate, the shrinkage deformation after final curing and the temporal deformation thereafter are less likely occurred. When the evaluation result of the green-state polymerization rate is 80(%) or more and the polymerization increase rate is 15(%) or less, the dental three-dimensional modeled object easily maintains its shape because the shrinkage deformation is not occurred from before the final curing to after the final curing. On the other hand, when the evaluation result of the green-state polymerization rate is less than 70(%) or the polymerization increase rate is 20(%) or more, the dental three-dimensional modeled object easily shrinks and deforms because polymerization proceeds remarkably from before the final curing and after the final curing. Based on these, in the stereolithography-type three-dimensional printing material according to the present invention, it is preferable that the evaluation result of the green-state polymerization rate is 70(%) or more and less than 80(%), or the polymerization increase rate is 15(%) or more and less than 20(%), further, it is particularly preferable that the evaluation result of the evaluation result of the green-state polymerization rate is 80(%) or more, and the polymerization increase rate is less than 15(%). Hereinafter, the criteria for determining the evaluation results of the green-state polymerization rate and the polymerization increase rate are described below.

Evaluation A: the evaluation result of the post-modeling polymerization rate is 80(%) or more and the polymerization increase rate is less than 15(%).

Evaluation B: the evaluation result of the evaluation result of the post-modeling polymerization rate is 70(%) or more and less than 80(%) or the polymerization increase rate is 15(%) or more and less than 20(%)

Evaluation C: the evaluation result of the post-modeling polymerization rate is less than 70(%) or more or the polymerization increase rate is more than 20(%).

(Measurement of Bending Strength)

By using a 3D printer (manufactured by DGSHAPE Corporation; DWP-80S), six rods of modeled objects having the dimension of 2.4 mm×2.4 mm×26 mm were obtained from the stereolithography-type three-dimensional printing material prepared under the modeling parameters of the laminate height of 50 µm per layer and the exposure time of 8 seconds. The obtained modeled objects were polished into the dimension of 2.0 mm×2.0 mm×26 mm by a water resistant polishing sheet #1200. By using the LC-3D print Box (manufactured by Nextdent B.V.) which is a post-curing device, the polished modeled objects was finally cured for 15 minutes to obtain six rods of test specimens for evaluation of the bending strength. The bending strength of the obtained test specimen for evaluation of the bending strength was measured with a universal testing machine Instron 5967 under the condition of a crosshead speed of 2 mm/min. The average value of the 6 rods of the test specimens for evaluation of the bending strength was used as the evaluation result of the bending strength.

The dental three-dimensional modeled object prepared by steps from stereolithography through final curing requires appropriate bending strength in accordance with each application. When the dental three-dimensional modeled object used as model, splint, mouth guard, night guard, surgical guide and cast for casting has a bending strength of 50 (MPa) or more, they do not break during clinical use and can be used for a long time. Based on these, in the stereolithography-type three-dimensional printing material according to the present invention, it is preferable that the evaluation result of bending strength is 50 (MPa) or more. The criteria for determining the evaluation result of bending strength are described below.

Evaluation A: 50 (MPa) or more
Evaluation B: less than 50 (MPa)

(Confirmation of Modeling Speed)

By using a 3D printer (manufactured by DGSHAPE Corporation; DWP-80 S), six pieces of modeled objects having the dimension of 20 mm×10 mm×5 mm were simultaneously obtained from the stereolithography-type three-dimensional printing material prepared under the modeling parameter of the laminate height of 200 µm per layer. When it was confirmed that all dimensional errors of obtained six pieces of modeled objects were within 1% from the desired data, the fastest modeling speed was used as the evaluation result of modeling speed.

The faster the modeling speed by a 3D printer, the more the work efficiency in stereolithography is excellent. Particularly, a dental three-dimensional modeled object such as a dental model requiring strict dimensional accuracy is generally modeled with a laminate height of 50 µm, and therefore has a problem that the modeling time is long. When a support is provided perpendicularly to the horizontal surface (back surface) of the dental model or when the dental model is directly attached to the platform without the support, the modeling height in the Z-axis direction is 20 to 25 mm. In case of setting the working time to 8 hours per a day, when the modeling time is kept within 4 hours under the parameter of laminate height of 50 µm, it is possible to model dental model the two or more times during the working time, which is excellent in working efficiency. On the other hand, when the modeling time exceeds 4 hours, the number of modeling times of the dental model prepared during working time is 1 or less and the productivity is insufficient. Based on these, in the stereolithography-typr three-dimensional printing material according to the present invention, it is preferable that the evaluation result of modeling speed with 200 µm laminate height is 25 (mm/hr) or more. The criteria for determining the evaluation result of modeling speed are described below.

Evaluation A: 25 (mm/hr) or more
Evaluation B: less than 25 (mm/hr)

(Measurement of Dimensional Change)

By using a 3D printer (manufactured by DGSHAPE Corporation; DWP-80 S), three pieces of modeled objects having the dimension of 20 mm (X direction)×10 mm (Y direction)×5 mm (Z direction) were obtained from the stereolithography-type three-dimensional printing material prepared under the modeling parameters of the laminate height of 50 µm per layer and the exposure time of 8 seconds. The dimensions of the obtained three modeled objects in the X, Y, and Z directions were measured with a digital caliper and recorded as a green-state dimension value. The modeled objects after measuring the green-state dimensions were finally cured for 15 minutes by the LC-3D print Box (manufactured by Nextdent B.V.) which is a post-curing device. The dimensions of the three finally cured modeled objects in the X, Y, and Z directions were measured with a digital caliper and recorded as a post-final curing dimension value. The dimensional change rate (%) was calculated by the following formula (V) from the green-state dimensional value and the corresponding post-final curing dimensional value corresponding, and the average value of all calculated dimensional change rates was used as the evaluation result of dimensional change.

Dimensional change rate (%)=(|dimension value green-state−dimension value post-final curing|/dimension value green-state)×100    formula (V)

In the dental three-dimensional modeled object prepared by steps from stereolithography through final curing, the closer the green-state dimension is to the post-final curing dimension, the shrinkage deformation after final curing and the temporal deformation thereafter are less likely occurred. When the evaluation result of dimensional change is 0.50 (%) or more, a shrinkage deformation of 25 μm or more occurs in the dental three-dimensional modeled object. For example, when shrinkage deformation of 25 μm or more occurs in the modeled dental models, as a result, there is a case that the cement space set in the crown prosthetic device is affected, and the fitting ability in the patient's oral cavity is reduced. Based on these, in the stereolithography-type three-dimensional printing material according to the present invention, it is preferable that the evaluation result of dimensional change is less than 0.50(%). The criteria for determining the evaluation results of dimensional change are described below.

Evaluation A: less than 0.50(%)
Evaluation B: 0.50(%) or more

TABLE 1

| Component | | Kind | Value in Formula (I) | Example (1) | Example (2) | Example (3) | Example (4) | Example (5) | Example (6) | Example (7) | Example (8) | Example (9) | Example (10) |
|---|---|---|---|---|---|---|---|---|---|---|---|---|---|
| Dental stereo-lithography-type three-dimensional printing material | (a) monofunctional acrylate monomer having aromatic ring | A-PP-EO | | 30 | | | | 30 | 30 | 97 | 77 | 67 | 50 |
| | | A-PE | | | 30 | | | | | | | | |
| | | A-PB | | | | 30 | | | | | | | |
| | | A-P2EG | | | | | 30 | | | | | | |
| | (c) polyfunctional methacrylate monomer | 2M-3EG | 14.96 | | | | | | | | | | |
| | | 2M-2.6EO | 16.59 | | | | | 67 | | | | | |
| | | 2M-1.0EO | 14.28 | | | | | | 67 | | | | |
| | | UDMA | 15.11 | 67 | 67 | 67 | 67 | | | | 20 | 30 | 47 |
| | Other monomer | A-PP-OH | | | | | | | | | | | |
| | | 2A-3cD | | | | | | | | | | | |
| | | M-PE | | | | | | | | | | | |
| | | 3A-IC | 27.16 | | | | | | | | | | |
| | (b) photopolymerization initiator | MAPO | | 3 | 3 | 3 | 3 | 3 | 3 | 3 | 3 | 3 | 3 |
| | Non-dendritic polymer | PEG1000 | | | | | | | | | | | |
| | | PPG4000 | | | | | | | | | | | |
| | Inorganic filler | R-812 | | | | | | | | | | | |
| | Coloring material | Titanium oxide | | | | | | | | | | | |
| | | Solvent Black 5 | | | | | | | | | | | |
| Evaluation result | Viscosity mPa·s) | | | 1918 | 356 | 689 | 458 | 714 | 706 | 160 | 198 | 229 | 539 |
| | Viscosity evaluation | | | A | A | A | A | A | A | A | A | A | A |
| | Green-state polymerization rate (%) | | | 83.9 (0.5) | 86.0 (0.7) | 86.2 (0.2) | 85.4 (0.9) | 72.3 (1.0) | 71.5 (0.8) | 93.5 (0.1) | 92.7 (0.1) | 92.6 (0.2) | 90.1 (0.1) |
| | Polymerizations increase rate (%) | | | 13.6 | 11.9 | 9.6 | 12 | 19.7 | 197 | 16 | 17 | 17 | 5.9 |
| | Polymerizations rate evaluation | | | A | A | A | A | B | B | A | A | A | A |
| | Bending strength (MPa) | | | 112 (2) | 101 (1) | 113 (1) | 50 (3) | 110 (4) | 80 (6) | 6 (1) | 18 (1) | 51 (5) | 70 (3) |
| | Bending strength evaluation | | | A | A | A | A | A | A | B | B | A | A |
| | Modeling speed (mm/hr) | | | 30 | 30 | 30 | 30 | 28 | 28 | 30 | 33 | 33 | 30 |
| | Modeling speed evaluation | | | A | A | A | A | A | A | A | A | A | A |
| | Dimensional change (%) | | | 0.20 (0.23) | 0.18 (0.33) | 0.16 (0.32) | 0.19 (0.33) | 0.47 (0.18) | 0.47 (0.29) | 0.22 (0.48) | 0.21 (0.33) | 0.22 (0.35) | 0.15 (0.39) |
| | Dimensional change evaluation | | | A | A | A | A | A | A | A | A | A | A |

TABLE 2

| Component | | Kind | Value in Formula (I) | Example (11) | Example (12) | Example (13) | Example (14) | Example (15) | Example (16) | Example (17) | Example (18) | Example (19) | Example (20) |
|---|---|---|---|---|---|---|---|---|---|---|---|---|---|
| Dental stereo-lithography-type three-dimensional printing material | (a) monofunctional acrylate monomer having aromatic ring | A-PP-EO | | 10 | 5 | 50 | 50 | 50 | 50 | 50 | 30 | 50 | 30 |
| | | A-PE | | | | | | | | | | | |
| | | A-PB | | | | | | | | | | | |
| | | A-P2EG | | | | | | | | | | | |
| | (c) polyfunctional methacrylate monomer | 2M-3EG | 14.96 | | | | | | | | 67 | | |
| | | 2M-2.6EO | 16.59 | | | | | | | | | | |
| | | 2M-4.0EO | 14.28 | | | | | | | | | | |
| | | UDMA | 15.11 | 87 | 92 | 45 | 49.5 | 47 | 47 | 47 | | 44 | 47 |
| | Other monomer | A-PP-OH | | | | | | | | | | | 20 |
| | | 2A-3cD | | | | | | | | | | | |
| | | M-PE | | | | | | | | | | | |
| | | 3A-IC | 27.16 | | | | | | | | | | |
| | (b) photopolymerization initiator | MAPO | | 3 | 3 | 5 | 0.5 | 3 | 3 | 3 | 3 | 6 | 3 |
| | Non-dendritic polymer | PEG1000 | | | | | | 7.5 | | | | | |
| | | PPG4000 | | | | | | | 7.5 | 7.5 | | | |
| | Inorganic filler | R-812 | | | | | | 2.5 | 2.5 | 2.5 | | | |
| | Coloring material | Titanium oxide | | | | | | 0.1 | 0.1 | | | | |
| | | Solvent Black 5 | | | | | | | | 0.02 | | | |
| Evaluation result | Viscosity mPa·s | | | 7832 | 16658 | 486 | 592 | 1112 | 1240 | 1233 | 10 | 472 | 2305 |
| | Viscosity evaluation | | | B | C | A | A | A | A | A | A | A | A |
| | Green-state polymerization rate (%) | | | 80.1 (0.4) | 77.8 (0.4) | 91.0 (0.1) | 86.9 (0.3) | 90.5 (0.2) | 90.8 (0.2) | 89.8 (0.2) | 83.3 (0.5) | 93 (0.5) | 83.1 (0.5) |
| | Polymerizations increase rate (%) | | | 116 | 119 | 6.0 | 9.6 | 65 | 5.6 | 63 | 11.7 | 3.2 | 113 |
| | Polymerizations rate evaluation | | | A | B | A | A | A | A | A | A | A | A |
| | Bending strength (MPa) | | | 136 (4) | 148 (6) | 73 (4) | 68 (3) | 60 (2) | 62 (3) | 56 (2) | 50 (2) | 62 (3) | 56 (2) |
| | Bending strength evaluation | | | A | A | A | A | A | A | A | A | A | A |
| | Modeling speed (mm/hr) | | | 28 | 27 | 33 | 25 | 30 | 30 | 25 | 33 | 35 | 27 |
| | Modeling speed evaluation | | | A | A | A | A | A | A | A | A | A | A |
| | Dimensional change (%) | | | 0.45 (0.29) | 0.13 (0.19) | 0.13 (0.31) | 0.30 (0.27) | 0.23 (0.43) | 0.13 (0.23) | 0.15 (0.44) | 0.21 (0.22) | 0.08 (0.23) | 0.28 (0.23) |
| | Dimensional change evaluation | | | A | A | A | A | A | A | A | A | A | A |

TABLE 3

| Component | | Kind | Value in Formula (I) | Comparative Example (1) | Comparative Example (2) | Comparative Example (3) | Comparative Example (4) | Comparative Example (5) |
|---|---|---|---|---|---|---|---|---|
| Dental stereo-lithography-type three-dimensional printing material | (a) monofunctional acrylate monomer having aromatic ring | A-PP-EO | | | | | | |
| | | A-PE | | | | | | |
| | | A-PB | | | | | | |
| | | A-P2EG | | | | | | |
| | (c) polyfunctional methacrylate monomer | 2M-3EG | 14.96 | 30 | 30 | | | |
| | | 2M-2.6EO | 16.59 | | | | | |
| | | 2M-4.0EO | 14.28 | | | | | |
| | | UDMA | 15.11 | 67 | 67 | 67 | 67 | |
| | Other monomer | A-PP-OH | | 30 | | | | |
| | | 2A-3cD | | | 30 | | | |
| | | M-PE | | | | 30 | | |
| | | 3A-IC | 27.16 | | | | | 67 |
| | (b) photopolymerization initiator | MAPO | | 3 | 3 | 3 | 3 | 3 |

TABLE 3-continued

| Component | | Kind | Value in Formula (I) | Comparative Example (1) | Comparative Example (2) | Comparative Example (3) | Comparative Example (4) | Comparative Example (5) |
|---|---|---|---|---|---|---|---|---|
| | Non-dendritic polymer | PEG1000 PPG4000 | | | | | | |
| | Inorganic filler | R-812 | | | | | | |
| | Coloring material | Titanium oxide | | | | | | |
| | | Solvent Black 5 | | | | | | |
| Evaluation result | Viscosity (mPa · s) | | | 2110 | 2160 | 338 | 354 | Crystallization |
| | Viscosity evaluation | | | A | A | A | A | C |
| | Green-state polymerization rate (%) | | | 81.2 (0.1) | 71.2 (0.9) | 79.2 (0.5) | 73.7 (1.0) | 60.1 (0.7) |
| | Polymerizations increase rate (%) | | | 15.2 | 22.2 | 16.8 | 22.1 | 29.5 |
| | Polymerizations rate evaluation | | | B | C | B | C | C |
| | Bending strength (MPa) | | | 89 (2) | 104 (2) | 101 (1) | 92 (1) | 91 (8) |
| | Bending strength evaluation | | | A | A | A | A | A |
| | Modeling speed (mm/hr) | | | 27 | 27 | 25 | 25 | 23 |
| | Modeling speed evaluation | | | A | A | A | B | B |
| | Dimensional change (%) | | | 0.54 (0.22) | 0.68 (0.34) | 0.50 (0.26) | 0.61 (0.37) | 0.79 (0.33) |
| | Dimensional change evaluation | | | B | B | B | B | B |

As shown in Tables 1 to 3, in Examples (1) to (6), (9), (10), (13), (14), (18) and (20) which contain "(a) monofunctional acrylate monomer having an aromatic ring", "(b) photopolymerization initiator", and "(c) polyfunctional methacrylate monomer" and in Examples (15) to (17) which contain "(a) monofunctional acrylate monomer having an aromatic ring", "(b) photopolymerization initiator", and "(c) polyfunctional methacrylate monomer" and at least one selected from a group consisting of a non-dendritic polymer containing no inorganic atom in the structure, an inorganic filler, and a coloring material, it was confirmed that all evaluation results were within the preferable range or particularly preferable range and these were an excellent stereolithography-type three-dimensional printing material.

In Example 19 which contains "(a) monofunctional acrylate monomer having an aromatic ring", "(b) photopolymerization initiator", and "(c) polyfunctional methacrylate monomer", although all evaluation results were within the preferable range or particularly preferable range, because releasability between the modeled product and the tank decreased, the modeled product frequently dropped. Therefore, it was confirmed that Example (19) is a stereolithography-type three-dimensional printing material which has suitable physical properties as the dental three-dimensional modeled object but is relatively likely to have modeling defects.

In Example (7) which contains "(a) monofunctional acrylate monomer having an aromatic ring" and "(b) photopolymerization initiator", and in Example (8) which contains "(a) monofunctional acrylate monomer having an aromatic ring", "(b) photopolymerization initiator", and "(c) polyfunctional methacrylate monomer", the evaluation result of bending strength were not within the preferable range, but the other evaluation results were excellent. Therefore, it was confirmed that Examples (7) and (8) were stereolithography-type three-dimensional printing materials with excellent work efficiency and small shrinkage deformation after final curing. It is considered that the printing materials as Examples (7) and (8) are suitable for a three-dimensional modeled object requiring flexibility.

In Examples (11) and (12) which contain "(a) monofunctional acrylate monomer having an aromatic ring", "(b) photopolymerization initiator", "(c) polyfunctional methacrylate monomer", the result of the viscosity evaluation was not within the preferable range, but the other evaluation results were excellent by controlling the temperature to reduce the viscosity to a preferable range or a particularly preferable range and thereafter modeling. Therefore, it was confirmed that the heated Examples (11) and (12) were stereolithography-type three-dimensional printing materials with excellent work efficiency and small shrinkage deformation after final curing, and not easily occurring breakage in the dental three-dimensional modeled object during clinical use. However, it was also confirmed that the surface of the three-dimensional modeled object after cleaning and after final curing was slightly sticky compared with the other examples, and therefore further studies such as an extension of cleaning time and final curing time were necessary.

In Comparative Example (1) using a monofunctional acrylate monomer (A-PP-OH) having the electronegativity difference between adjacent atoms which are bonded by covalent bond of 1.0 or more and an aromatic ring instead of the "(a) monofunctional acrylate monomer having an aromatic ring", the evaluation result of dimensional change was not within the preferable range. Therefore, it was confirmed that Comparative Example (1) was the stereolithography-type three-dimensional printing material with a large shrinkage deformation after final curing.

In Comparative Example (2) using a difunctional acrylate monomer (2A-3cD) having the electronegativity difference between adjacent atoms which are bonded by covalent bond of less than 1.0 and no aromatic ring instead of the "(a) monofunctional acrylate monomer having an aromatic ring", the evaluation results of polymerization increase rate and dimensional change were not within the preferable ranges. Therefore, it was confirmed that Comparative Example (2)

was the stereolithography-type three-dimensional printing material with a large shrinkage deformation after final curing.

In Comparative Example (3) using a monofunctional methacrylate monomer (M-PE) having the electronegativity difference between adjacent atoms which are bonded by covalent bond of less than 1.0 and aromatic ring instead of the "(a) monofunctional acrylate monomer having an aromatic ring", the evaluation result of dimensional change was not within the preferable ranges. Therefore, it was confirmed that Comparative Example (3) was the stereolithography-type three-dimensional printing material with a large shrinkage deformation after final curing.

In Comparative Example (4) including only "(c) polyfunctional methacrylate monomer" in the monomer composition, the evaluation results of polymerization increase rate, modeling speed and dimensional change were not within the preferable ranges. Therefore, it was confirmed that Comparative Example (4) was the stereolithography-type three-dimensional printing material with a large shrinkage deformation after final curing and lacking in work efficiency.

In Comparative Example (5) including only the "(c) polyfunctional methacrylate monomer" and the polyfunctional methacrylate monomer (3A-IC) having the value calculated from the formula (I) of more than 20 in the monomer composition, the evaluation result of the viscosity, the green-state polymerization rate, polymerization increase rate, modeling speed, and dimensional change were not within preferable ranges. Comparative Example (5) was able to be modeled by lowering the viscosity to a preferable range or a particularly preferable range by controlling the temperature, but it was confirmed that it was the stereolithography-type three-dimensional printing material with a large shrinkage deformation after final curing and a lack of work efficiency. Furthermore, since the stereolithography-type three-dimensional printing material was crystallized under the condition of 23° C., it was necessary to wash immediately after the modeling before the liquid material on the surface of the three-dimensional modeled object is crystallized.

With respect to the use of substantially any plural and/or singular terms herein, those having skill in the art can translate from the plural to the singular and/or from the singular to the plural as is appropriate to the context. Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The dental stereolithography-type three-dimensional printing material of the present invention is used for preparing a modeled object having three-dimensional shape used in a dentistry by a 3D printer.

What is claimed is:

1. A dental stereolithography-type three-dimensional printing material comprising at least one or more (a) monofunctional acrylate monomer having an aromatic ring and (b) photopolymerization initiator, wherein
    an electronegativity difference between adjacent atoms which are bonded by covalent bond in all atoms constituting the (a) monofunctional acrylate monomer having an aromatic ring is less than 1.0.

2. The dental stereolithography-type three-dimensional printing material according to claim 1, wherein
    the content of the (b) photopolymerization initiator is within a range of 0.1 to 5 wt. %.

3. The dental stereolithography-type three-dimensional printing material according to claim 2, wherein
    the dental stereolithography-type three-dimensional printing material further comprises at least one selected from a group consisting of a non-dendritic polymer containing no inorganic atom in the structure, an inorganic filler, and a coloring material.

4. The dental stereolithography-type three-dimensional printing material according to claim 3, wherein
    the dental stereolithography-type three-dimensional printing material has a viscosity (mPa·s) at 23° C. within a range of 1 to less than 3000.

5. The dental stereolithography-type three-dimensional printing material according to claim 2, wherein
    the dental stereolithography-type three-dimensional printing material has a viscosity (mPa·s) at 23° C. within a range of 1 to less than 3000.

6. The dental stereolithography-type three-dimensional printing material according to claim 1, wherein
    the dental stereolithography-type three-dimensional printing material further comprises (c) polyfunctional methacrylate monomer wherein
    an electronegativity difference between adjacent atoms which are bonded by covalent bond in all atoms constituting the (c) polyfunctional methacrylate monomer is less than 1.0, and
    the (c) polyfunctional methacrylate monomer satisfies the following formula (I)

$$\text{Molecular weight/molecular length when both ends of the monomer molecule are methacrylate groups (angstrom)} < 20.0 \quad \text{Formula (I)}.$$

7. The dental stereolithography-type three-dimensional printing material according to claim 6, wherein
    the dental stereolithography-type three-dimensional printing material comprises, based on the total weight of the (a) monofunctional acrylate monomer having an aromatic ring, the (b) photopolymerization initiator and the (c) polyfunctional methacrylate monomer,
(a) monofunctional acrylate monomer having an aromatic ring: 10 to 70 wt. %,
(b) photopolymerization initiator: 0.1 to 5 wt. %, and
(c) polyfunctional methacrylate monomer: 25 to 89.9 wt. %.

8. The dental stereolithography-type three-dimensional printing material according to claim 7, wherein
    the dental stereolithography-type three-dimensional printing material further comprises at least one selected from a group consisting of a non-dendritic polymer containing no inorganic atom in the structure, an inorganic filler, and a coloring material.

9. The dental stereolithography-type three-dimensional printing material according to claim 8, wherein
    the dental stereolithography-type three-dimensional printing material has a viscosity (mPa·s) at 23° C. within a range of 1 to less than 3000.

10. The dental stereolithography-type three-dimensional printing material according to claim 7, wherein
    the dental stereolithography-type three-dimensional printing material has a viscosity (mPa·s) at 23° C. within a range of 1 to less than 3000.

11. The dental stereolithography-type three-dimensional printing material according to claim 6, wherein
the dental stereolithography-type three-dimensional printing material further comprises at least one selected from a group consisting of a non-dendritic polymer containing no inorganic atom in the structure, an inorganic filler, and a coloring material.

12. The dental stereolithography-type three-dimensional printing material according to claim 11, wherein
the dental stereolithography-type three-dimensional printing material has a viscosity (mPa·s) at 23° C. within a range of 1 to less than 3000.

13. The dental stereolithography-type three-dimensional printing material according to claim 6, wherein
the dental stereolithography-type three-dimensional printing material has a viscosity (mPa·s) at 23° C. within a range of 1 to less than 3000.

14. The dental stereolithography-type three-dimensional printing material according to claim 1, wherein
the dental stereolithography-type three-dimensional printing material further comprises at least one selected from a group consisting of a non-dendritic polymer containing no inorganic atom in the structure, an inorganic filler, and a coloring material.

15. The dental stereolithography-type three-dimensional printing material according to claim 14, wherein
the dental stereolithography-type three-dimensional printing material has a viscosity (mPa·s) at 23° C. within a range of 1 to less than 3000.

16. The dental stereolithography-type three-dimensional printing material according to claim 1, wherein
the dental stereolithography-type three-dimensional printing material has a viscosity (mPa·s) at 23° C. within a range of 1 to less than 3000.

17. A preparing method of a dental three-dimensional modeled object, wherein
the method does not comprise a step of a final curing, by a light and/or heating type post-curing device, a dental three-dimensional modeled object modeled by stereolithography-type three-dimensional printing machine using the dental stereolithography-type three-dimensional printing material according to claim 1.

* * * * *